United States Patent
Haines et al.

(10) Patent No.: US 6,385,473 B1
(45) Date of Patent: May 7, 2002

(54) PHYSIOLOGICAL SENSOR DEVICE

(75) Inventors: Paul D. Haines; Andrea J. Harry; Harpal S. Kumar, all of Cambridge; John D. Place, Suffolk, all of (GB); Susan B. Riley Earl, Sausalito, CA (US); Neil J. Sheehan, Palo Alto, CA (US); David A. Sheraton, Irvine, CA (US)

(73) Assignee: Nexan Limited, Cambridge (GB)

( * ) Notice: Subject to any disclaimer, the term of this patent is extended or adjusted under 35 U.S.C. 154(b) by 0 days.

(21) Appl. No.: 09/292,157

(22) Filed: Apr. 15, 1999

(51) Int. Cl.$^7$ .............................................. A61B 5/0478
(52) U.S. Cl. ........................ 600/393; 600/382; 600/391; 600/392
(58) Field of Search ................................ 600/372, 382, 600/384, 386–397, 509; 607/152

(56) References Cited

U.S. PATENT DOCUMENTS

| 2,298,125 A | 10/1942 | Hartman | ..................... 128/2.1 |
| 2,660,165 A | 11/1953 | Miller | ....................... 128/2.06 |

(List continued on next page.)

FOREIGN PATENT DOCUMENTS

| CH | 293560 | 12/1953 |
| EP | 0 212 278 | 3/1987 |
| EP | 0 479 857 B1 | 12/1993 |
| EP | 0 617 914 A1 | 10/1994 |
| EP | 0 458 883 B1 | 11/1996 |
| EP | 0 760 224 A1 | 3/1997 |
| EP | 0 761 160 A1 | 3/1997 |
| EP | 0 770 349 A1 | 5/1997 |
| EP | 0 719 108 B1 | 6/1997 |
| EP | 0 796 589 A1 | 9/1997 |
| EP | 0 796 590 A1 | 9/1997 |
| EP | 0 598 016 B1 | 10/1997 |
| GB | 2 003 276 A | 3/1979 |
| GB | 2 207 579 A | 2/1989 |
| WO | WO 87/06447 | 11/1987 |
| WO | WO 90/01898 | 3/1990 |
| WO | WO 91/00054 | 1/1991 |
| WO | WO 9302622 | 2/1993 |

(List continued on next page.)

OTHER PUBLICATIONS

"Microcomputer–based Telemetry System for ECG Monitoring," Proceedings of the Ninth Annual Conference of the IEEE Engineering in Medicine and Biology Society, The Boston Park Plaza Hotel, Boston, MA, Nov. 13–16, 1987, vol. 3 of 4, 2 pages.

"Biomedical Telectrodes: Compact transmitters would eliminate the need for wires to monitors," NASA TechBrief, Lyndon B. Johnson Space Center, Houston, Texas, Feb. 1990, 1 page.

Primary Examiner—Linda C. M. Dvorak
Assistant Examiner—David M. Ruddy
(74) Attorney, Agent, or Firm—Woodcock Washburn LLP (57) ABSTRACT

A physiological sensor device for attachment to a mammalian subject including first and second regions of sensors attachable to a subject in use, which first and second regions of sensors are separated by a flexible web adapted to enable variable separation of the first and second sensor regions from one another in use. The physiological sensor device is manufactured by forming a strip of electrically conductive material on a flexible electrically non-conductive substrate and cutting a slot through both the flexible substrate and conductive strip to define a pair of adjacent edges of conductive material separated by a non-conductive gap thereby also to define adjacent electrode sensors each having one of the pair of adjacent edges formed in the strip of conductive material. The physiological sensor device is attached to the subject for measurement of numerous physiological parameters for a period of time, such as 24 hours, and is then thrown away.

37 Claims, 4 Drawing Sheets

U.S. PATENT DOCUMENTS

| | | | |
|---|---|---|---|
| 3,212,496 A | 10/1965 | Preston | 128/2.06 |
| 3,409,007 A | 11/1968 | Fuller | 128/2.06 |
| 3,572,316 A | 3/1971 | Vogelman et al. | 128/2.05 |
| 3,572,322 A | 3/1971 | Wade | 128/2.06 |
| 3,603,881 A | 9/1971 | Thornton | 325/30 |
| 3,757,778 A | 9/1973 | Graham | 128/2.06 R |
| 3,848,582 A | 11/1974 | Milani et al. | 128/2.06 R |
| 3,858,576 A | 1/1975 | Dehnert et al. | 128/2.06 R |
| 3,882,277 A | 5/1975 | DePedro et al. | 179/2 DP |
| 3,902,478 A | 9/1975 | Konopasek et al. | 128/20.6 F |
| 3,908,641 A | 9/1975 | Judson et al. | 128/20.6 G |
| 3,943,918 A | 3/1976 | Lewis | 128/2.1 A |
| 3,986,498 A | 10/1976 | Lewis | 128/2.06 R |
| 4,023,564 A | 5/1977 | Valiquette et al. | 128/2.06 A |
| 4,082,087 A | 4/1978 | Howson | 128/2.06 E |
| 4,121,573 A | 10/1978 | Crovella et al. | 128/2.1 A |
| 4,121,575 A | 10/1978 | Mills et al. | 128/2.06 E |
| 4,122,843 A | 10/1978 | Zdrojkowski | 128/2.06 E |
| 4,141,351 A | 2/1979 | James et al. | 128/2.06 R |
| 4,202,344 A | 5/1980 | Mills et al. | 128/644 |
| 4,233,987 A | 11/1980 | Feingold | 128/639 |
| 4,249,538 A | 2/1981 | Musha et al. | 128/630 |
| 4,319,241 A | 3/1982 | Mount | 128/870.38 |
| 4,328,814 A | 5/1982 | Arkans | 128/640 |
| 4,353,372 A | 10/1982 | Ayer | 128/640 |
| 4,356,486 A | 10/1982 | Mount | 340/870.38 |
| 4,494,553 A | 1/1985 | Sciarra et al. | 128/721 |
| 4,522,211 A | 6/1985 | Bare et al. | 128/640 |
| 4,593,284 A | 6/1986 | Clifford et al. | 340/870.18 |
| 4,606,352 A | 8/1986 | Geddes et al. | 128/702 |
| 4,622,979 A | 11/1986 | Katchis et al. | 128/702 |
| 4,658,831 A | 4/1987 | Reinhard et al. | 128/697 |
| 4,662,378 A | 5/1987 | Thomis | 128/644 |
| 4,674,511 A * | 6/1987 | Cartmell | 128/640 |
| 4,709,704 A | 12/1987 | Lukasiewicz | 128/644 |
| 4,742,831 A | 5/1988 | Silvian | 128/710 |
| 4,763,660 A | 8/1988 | Kroll et al. | 128/640 |
| 4,787,162 A | 11/1988 | Ricks et al. | 128/903 |
| 4,827,943 A | 5/1989 | Bornn et al. | 128/668 |
| 4,852,572 A | 8/1989 | Nakahashi et al. | 128/640 |
| 4,893,632 A | 1/1990 | Armington | 128/696 |
| 4,909,260 A | 3/1990 | Salem et al. | 128/721 |
| 4,926,868 A | 5/1990 | Larsen | 128/653 R |
| 4,955,381 A | 9/1990 | Way et al. | 128/640 |
| 4,957,109 A | 9/1990 | Groeger et al. | 128/640 |
| 4,967,748 A | 11/1990 | Cohen | 128/419 D |
| 4,967,749 A | 11/1990 | Cohen | 128/419 PG |
| 4,981,141 A | 1/1991 | Segalowitz | 128/696 |
| 4,984,572 A | 1/1991 | Cohen | 128/419 D |
| 4,986,270 A | 1/1991 | Cohen | 128/419 D |
| 5,027,816 A | 7/1991 | Cohen | 128/419 PG |
| 5,038,782 A | 8/1991 | Gevins et al. | 128/644 |
| 5,050,612 A | 9/1991 | Matsumura | 128/670 |
| 5,069,215 A | 12/1991 | Jadvar et al. | 128/642 |
| 5,078,134 A | 1/1992 | Heilman et al. | 128/421 |
| 5,080,099 A | 1/1992 | Way et al. | 128/640 |
| 5,163,429 A | 11/1992 | Cohen | 128/419 PG |
| 5,168,874 A | 12/1992 | Segalowitz | 128/639 |
| 5,199,433 A | 4/1993 | Metzger et al. | 128/642 |
| 5,224,485 A | 7/1993 | Powers et al. | 128/696 |
| 5,228,449 A | 7/1993 | Christ et al. | 128/691 |
| 5,269,301 A | 12/1993 | Cohen | 607/6 |
| 5,279,305 A | 1/1994 | Zimmerman et al. | 128/731 |
| 5,307,817 A | 5/1994 | Guggenbuhl et al. | 128/696 |
| 5,307,818 A | 5/1994 | Segalowitz | 128/696 |
| 5,341,806 A * | 8/1994 | Gadsby et al. | 128/640 |
| 5,343,860 A | 9/1994 | Metzger et al. | 128/642 |
| 5,353,793 A | 10/1994 | Bornn | 128/642 |
| 5,372,125 A | 12/1994 | Lyons | 128/64 D |
| 5,373,852 A | 12/1994 | Harrison et al. | 128/733 |
| 5,394,882 A | 3/1995 | Mawhinney | 128/721 |
| 5,431,171 A | 7/1995 | Harrison et al. | 128/698 |
| 5,456,682 A | 10/1995 | Edwards et al. | 606/31 |
| 5,458,124 A | 10/1995 | Stanko et al. | 128/696 |
| 5,462,051 A | 10/1995 | Oka et al. | 128/630 |
| 5,464,021 A * | 11/1995 | Birnbaum | 128/696 |
| 5,465,715 A | 11/1995 | Lyons | 128/640 |
| 5,511,553 A | 4/1996 | Segalowitz | 128/696 |
| 5,522,396 A | 6/1996 | Langer et al. | 128/696 |
| 5,538,005 A | 7/1996 | Harrison et al. | 128/698 |
| 5,544,661 A | 8/1996 | Davis et al. | 128/700 |
| 5,549,113 A | 8/1996 | Halleck et al. | 128/671 |
| 5,558,638 A | 9/1996 | Evers et al. | 604/66 |
| 5,564,429 A | 10/1996 | Bornn et al. | 128/696 |
| 5,579,001 A | 11/1996 | Dempsey et al. | 340/870.01 |
| 5,579,775 A | 12/1996 | Dempsey et al. | 128/670 |
| 5,617,871 A | 4/1997 | Burrows | 128/696 |
| 5,634,468 A | 6/1997 | Platt et al. | 128/696 |
| 5,652,570 A | 7/1997 | Lepkofker | 340/573 |
| 5,660,177 A | 8/1997 | Faupel et al. | 128/639 |
| 5,670,944 A | 9/1997 | Myllymäki | 340/573 |
| 5,678,545 A | 10/1997 | Stratbucker | 128/640 |
| 5,682,902 A | 11/1997 | Herleikson | 128/708 |
| 5,687,737 A | 11/1997 | Dempsey et al. | 128/696 |
| 5,733,151 A * | 3/1998 | Edsall et al. | 439/729 |
| 5,746,207 A | 5/1998 | McLaughlin et al. | 128/639 |
| 5,891,044 A | 4/1999 | Golosarsky et al. | 600/509 |
| 6,006,125 A * | 12/1999 | Kelly et al. | 600/382 |
| 6,032,064 A * | 2/2000 | Devlin et al. | 600/383 |
| 6,032,065 A * | 2/2000 | Brown | 600/383 |
| 6,055,448 A | 4/2000 | Anderson et al. | 600/372 |
| 6,076,003 A * | 6/2000 | Rogel | 600/390 |
| 6,128,521 A * | 10/2000 | Marro et al. | 600/391 |

FOREIGN PATENT DOCUMENTS

| | | |
|---|---|---|
| WO | WO 93/08734 | 5/1993 |
| WO | WO 93/10706 | 6/1993 |
| WO | WO 93/19667 | 10/1993 |
| WO | WO 94/01039 | 1/1994 |
| WO | WO 94/03105 | 2/1994 |
| WO | WO 94/25841 | 11/1994 |
| WO | WO 95/07048 | 3/1995 |
| WO | WO 95/07652 | 3/1995 |
| WO | WO 95/10974 | 4/1995 |
| WO | WO 96/01585 | 1/1996 |
| WO | WO 96/29005 | 9/1996 |
| WO | WO 96/38080 | 12/1996 |
| WO | WO 97/09923 | 3/1997 |
| WO | WO 97/28736 | 8/1997 |
| WO | WO 97/40747 | 11/1997 |

* cited by examiner

PHYSIOLOGICAL SENSOR DEVICE

BACKGROUND OF THE INVENTION

1. Field of the Invention

The present invention relates to a device for attachment to a mammalian subject in order to obtain data about one or more physiological parameters of the subject. In particular, the device relates to a physiological sensor device in the form of a patch attachable to the chest of a human subject to enable sensing of physiological data such as electrocardiographic data and/or respiration data, and a method of manufacture thereof

2. Description of the Prior Art

The prior art includes U.S. Pat. No. 3,943,918 to Lewis which discloses an ECG signal sensing and transmitting device for use in the care of medical patients requiring monitoring of cardiac functions. The device disclosed is a single use, disposable unit consisting principally of a foam pad having a pair of circular electrodes in one face of the rectangular foam block. The block is attached using an adhesive layer to a patient and comprises electrical circuitry which transmits an RF signal to a receiver which is required to be within 100 feet of the patient. Subsequent filtering and amplification of the signal takes place at a monitoring station comprising a receiver and filter.

U.S. Pat. No. 4,121,573 discloses a chest sensor for monitoring cardiac rhythms of a patient using a pair of spaced circular electrodes mounted on a foam pad. Electrical connectors between the electrodes and electronic circuitry for acquiring and transmitting cardiac rhythm signals is provided by independent electrical leads or wires. The circuitry and wires are located on the rear surface of a first layer of foam and held in position by a second layer of foam. Accordingly, a fairly deep configuration of layers of foam, electronic circuitry and electrodes is provided. A radio frequency receiver and converter is provided within the vicinity of the transmitter which passes a signal to display equipment for enabling a user to view the cardiac rhythms of the patient.

U.S. Pat. No. 4,957,109 discloses an electrode array for use in generating electrocardiographic signals for a patient. The array comprises ten different electrode regions (comprises pairs of semi-circular electrodes) for attachment to different parts of the human body. The electrodes are interconnected to an output connector 2 for attachment to signal processing apparatus. The electrode sensors and electrical conductors between the electrodes and the output conductor are formed on a flexible circuit board having a large dentritic or tree-like configuration to enable location of the electrodes at the appropriate positions on the human body for standard twelve lead diagnostic electrocardiogram studies. Accordingly, electrical connection from one electrode through to the output connector passes around one or more different electrode sensors on the flexible circuit board requiring a complicated arrangement of insulating material in order to try to prevent short circuiting between a sensor and surrounding electrical connections.

U.S. Pat. No. 5,634,468 discloses a sensor for physiological monitoring of a patient, consisting of a rectangular patch having a central structural member formed of MYLAR™ encased in an adhesive hydrogel. One side of the sensor has four circular electrodes for contacting the patient. The electrodes are wired to an electronic package on the opposite side of the structural member. The electronics package is adapted to receive ECG data and transmits the data to a monitoring unit. Such a small sensor is limited to measuring ECG signals.

U.S. Pat. No. 5,353,793 discloses sensor apparatus for making ECG measurements comprising a band which passes entirely round a patient's chest. The chest band can have optional shoulder straps and an optional abdominal band. Electrodes are positioned around the inner circumferential surface of the band for monitoring respiration, pulse and ECG signals. The ECG electrodes are simple conductive sensors in electrical contact with the skin. The pulse and respiration sensor comprises a tension sensor consisting of a piezoelectric element. A minimum of 7 ECG sensors is provided but up to 18 can be spaced around the band. Two or more of the piezoelectric sensors can be provided in a single chest band. The various sensors are connected by cabling and accordingly the apparatus as a whole is considerably bulky to wear.

International patent specification WO94/01039 discloses physiological monitoring apparatus having a strip assembly for attachment to a patient's chest. The strip comprises a series of nine electrically conductive electrode sensors for attachment to the precordial region of a patient's chest for obtaining ECG data. The strip is relatively complex and comprises a plurality of recesses for individual electrodes for example.

SUMMARY OF THE INVENTION

An object of the invention is to avoid or at least mitigate problems of the prior art. In particular, the invention seeks to provide an improved physiological sensor device which is easy to attach to a subject and/or comfortable to wear and/or disposable after a single use over, for example, a 24 hour period. Another object is to provide a device which is relatively simple to manufacture while enabling collection of accurate data. A further object of the invention is to provide a device which is able to collect a variety of types of physiological data, such as ECG, respiration, motion and temperature, for example, while still being relatively inexpensive to manufacture.

A first aspect of the invention provides a physiological sensor device for attachment to a mammalian subject comprising two regions of sensors attachable to a subject in use, which regions are separated by a flexible web adapted to enable variable separation of the two sensor regions from one another in use. Beneficially, the two sensor regions are attachable in precordial positions, substantially horizontally aligned, on a human chest, and the flexible web enables the subject to breathe and move easily after attachment of the device, in spite of expansion and reduction in chest size when breathing or moving.

Preferably the web comprises an outer layer which operably contacts a subject which layer does not adhere to the subject in use thereby to aid the increased flexibility of the device. Preferably, when unbiased, the flexible web has a neutral position which fixes the separation of the first and second sensor regions to a predetermined length. The flexible web further comprises a position indicator such as a substantially V-shaped portion. The V-shaped portion can be formed of two arms which subtend an angle of between of 60 and 130° and more preferably between 100 and 120°, and in one form an angle of 115°. The separation of the first and second regions in the unbiased position of the web can be between 20 and 200 mm and more preferably between 40 and 130 mm.

A third region of sensors attachable to the subject can be provided which region is separated from one of the first region and second region by a second flexible web. The second flexible web preferably also does not adhere to the subject in use. The third region can be adapted to attach below the axilla of a subject. Accordingly, the second web can be adapted to pass over the pectoral region of the subject. Preferably the length of the second web in the mutual unbiased position is between 20 and 200 mm and more preferably between 50 and 10 mm. The second web can subtend an angle to the first or second region of between 30 and 60° and more preferably about 45°.

Preferably, electrode sensors on the first region and second region are aligned on a transverse axis across both the first and second regions. This provides benefits in the ease of manufacture of the device as described later.

In another embodiment, a physiological sensor device can be provided for attachment to a mammalian subject comprising a first and second electrode sensor in spaced separation along the transverse axis of a region of the device, wherein the first and second electrode sensors are mounted on a flexible substrate.

The first and second electrode sensors can comprise electrically conductive ink printed on a flexible substrate. Preferably, the conductive ink is substantially non-polarizing and may comprise, for example, a silver/silver chloride ink.

The first and second electrode sensors are separated by a slot in the flexible substrate. A strip of conductive gel can be positioned over the first and second electrode sensors which conductive gel is also divided by a slot passing therethrough.

Another form of the invention provides a physiological sensor device for attachment to a mammalian subject comprising a region having at least one physiological sensor and a layer of adhesive for attachment of the region to the subject in use, wherein the region comprises at least one slot enabling greater flexibility in the region when worn by the subject in use.

A yet further aspect of the invention provides a physiological sensor device for attachment to a mammalian subject comprising an electrode sensor comprising a region having at least one electrode sensor comprising a layer of electrically conductive gel attachable to the subject in use, the region further comprising a layer of non-conductive adhesive also attachable to the subject in use. Preferably the electrically conductive gel also has adhesive properties. The gel can for example be a hydrogel, while the non-conductive adhesive can, for example, be hydrocolloid. In a preferred embodiment, two strips of non-conductive adhesive are provided adjacent opposite sides of a strip of electrically conductive gel.

A further aspect of the invention provides a physiological sensor device comprising a region having one or more sensors attachable close to a subject's axilla wherein the region comprises electrical circuitry for processing physiological signals from the one or more sensors. Preferably, the region comprises an output transmitter, such as a substantially flat coil antenna, for communicating the physiological signals to a remote location. Preferably, one of the sensors comprises a temperature sensor. Beneficially, this region can carry electrical circuitry for processing physiological signals from the one or more sensors and can be accommodated in the space between the wearer's chest and arm.

According to a further aspect of the invention there is provided a method of manufacturing a physiological sensor device having two or more electrode sensors, comprising the steps of forming a strip of electrically conductive material on a flexible electrically non-conductive substrate, and cutting a slot through both the flexible substrate and conductive strip to define a pair of adjacent edges of conductive material separated by a non-conductive gap thereby also to define adjacent electrode sensors each having one of said pair of adjacent edges formed in the strip of conductive material.

Preferably the step of forming a strip of conductive material comprises printing a layer of conductive ink onto the flexible non-conductive substrate. The method can comprise the step of laying a strip of electrically conductive gel over the strip of electrically conductive material prior to the step of cutting a slot therethrough.

Another aspect of the invention provides a method of manufacturing a physiological sensor device having a plurality of electrode sensors, comprising the steps of forming a series of electrode sensors axially separated one from another along a common axis, forming a layer of conductive gel over all the axially aligned electrode sensors using a single strip of conductive gel, and forming separate areas of gel over each sensor by cutting through the layer of gel between each of the electrode sensors in the series. Preferably the method further comprises the step of providing electrical isolation between one or more of the electrode sensors in the series by cutting slots in the flexible substrate to which the electrodes are mounted.

A further aspect of the invention provides a physiological sensor device for attachment to a mammalian subject, having a laminate structure comprising:

a flexible non-conductive substrate, an arrangement of electrically conductive tracks formed on the substrate,     an electrical device such as a physiological sensor or electronic circuit (PCB), electrically conducted to one or more of the electrically conductive tracks by an electrically conductive adhesive, and     a backing layer covering at least part of the arrangement of conductive tracks and attached to at least part of the flexible non-conductive substrate.

Preferably the conductive adhesive has a relatively low electrical resistance in one direction and a relatively high electrical resistance orthogonal thereto.

A yet further aspect of the invention provides a method of attaching a physiological sensor device comprising a patch attachable to a subject, which patch comprises a first and a second sensor region, separated by a flexible web, comprising the step of positioning the first sensor region in a precordial position on the chest and positioning the web over the subject's sternum thereby to locate the second sensor region on the right side of the subject's chest.

A yet further aspect of the invention provides a method of attaching a physiological sensor device comprising a patch attachable to a subject, which patch comprises a first sensor region attachable to a precordial position on a subject's chest, and another sensor region attachable to below the subject's axilla, where the first and another sensor region are separated by a flexible web, comprising the step of positioning the another sensor region below the subject's axilla and then positioning the first sensor region in a precordial position on the subject's chest by passing the flexible web over the subject's pectoral muscle. Preferably, the web comprises a position indicator and the method comprises the step of positioning the position indicator centrally on the sternum prior to attachment of the first and second sensor regions to the chest.

Also, the device can comprise a third sensor region separated from one of the first and second sensor regions by a second flexible web, the method further comprising the step of locating the third sensor region below the subject's axilla and passing the second flexible web over the subject's pectoral muscle. Preferably, the first, second and third sensor regions each comprise an electrode for measuring ECG and wherein the method of attachment of the three sensor regions enables the electrodes to be positioned on a subject in use so as to approximate an ECG lead II for ECG signal acquisition.

Another aspect of the invention provides a method of attaching a physiological sensor device comprising a patch attachable to a subject, which patch comprises a first sensor region attachable to a precordial position on a subject's chest, and another sensor region attachable to below the subject's axilla which first and another sensor region are separated by a flexible web, comprising the step of positioning another sensor region below the subject's axilla and then positioning the first sensor region in a precordial position on the subject's chest by passing the flexible web over the subject's pectoral muscle.

Other inventive features of the invention will become apparent from the following description. Moreover, the invention provides a device, method of manufacture thereof, or method of attachment thereof to a user comprising any one of the individual features herein described (including any individual parameter within any specified ranges) or any combination thereof.

BRIEF DESCRIPTION OF THE DRAWINGS

The invention will now be described, by way of example only, with reference to the accompanying drawings, in which.

DETAILED DESCRIPTION OF THE PRESENTLY PREFERRED EMBODIMENT

Figure 1:
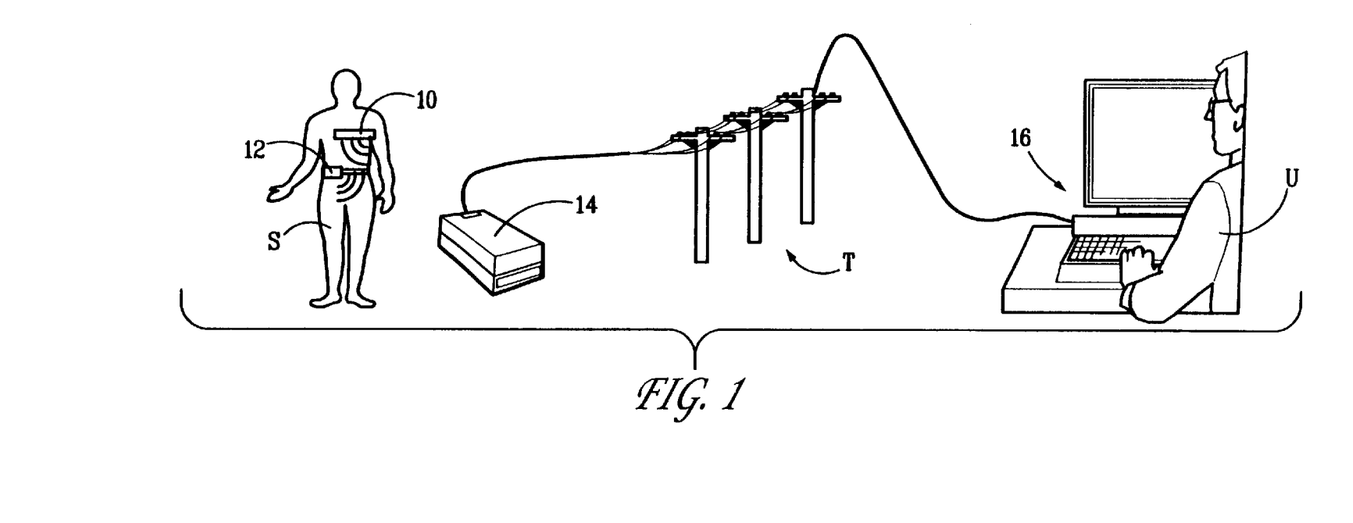
FIG. 1 is a schematic diagram of a physiological monitoring system in which a sensor device according to the invention can be suitably used.

FIG. 1 illustrates a physiological sensor device or array 10 according to the invention which is attached to the chest of a human subject or patient S. Device 10 comprises an array of sensors 10a (to be described later) which generatedata about the physiological condition of the subject. This data is transmitted to a portablesignal transfer unit 12. In turn, signal transfer unit 12 transmits a signal representative of the measured physiological parameters to a base station 14 which operably communicates with a remote monitoring station 16, which can comprise a suitably programmed computer 16b for example, via a telemetry or telephonic link T, such as a land based telephone system for example, using modems 14c and 16a.

Figure 2:
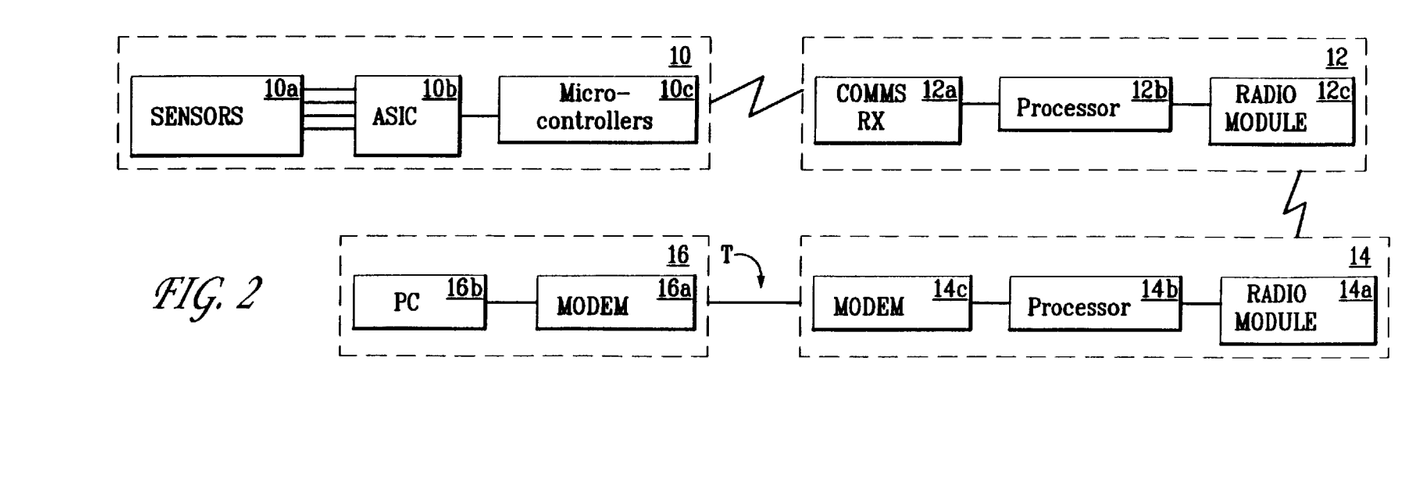
FIG. 2 is a schematic block diagram of the system shown in FIG. 1.

The basic structure of the different components in the system is shown in a schematic block diagram in FIG. 2. As can be seen, device 10 comprises an array of sensors 10a in communication with suitable electronics forming a controller for processing and communicating physiological data to the signal transfer unit 12. In this example, device 10 comprises an application specific integrated circuit (ASIC) 10b, and a communications programmable integrated circuit, COMMS PIC or micro-controller 10c. Further details of the preferred form of electronics and details of the sensors are given in our co-pending patent application entitled "Physiological Sensor Array", U.S. patent application Ser. No. 09/292,159, which is incorporated herein by reference in its entirety.

The system further comprises a portable signal transfer unit 12 having a receiver 12a in communication with a processor 12b which in turn enables two-way transfer of data and commands to base station 14 via a radio module 12c. Further details of a preferred form of unit 12 are given in our co-pending patent application entitled "Portable Signal Transfer Unit", U.S. patent application Ser. No. 09/292,158, which is incorporated herein by reference in its entirety.

Base station unit 14 comprises a radio module 14a for receiving data signals from signal transfer unit 12 and, a processor 14b suitably programmed to manipulate the physiological data and to enable transfer from base station 14 to remote monitoring station 16 via a modem 14c and a link T. Remote monitoring station 16 comprises a modem 16a and programmable computer 16b, for example. Further details of the base station 14 and remote monitoring station 16 as well as the system as a whole, including details of the format of transmitted data and transmission protocols between the device 10 and unit 12, are given in our co-pending application entitled "Portable Remote Patient Telemonitoring System", U.S. patent application Ser. No. 09/292,405, which is incorporated herein by reference in its entirety.

Figure 3:
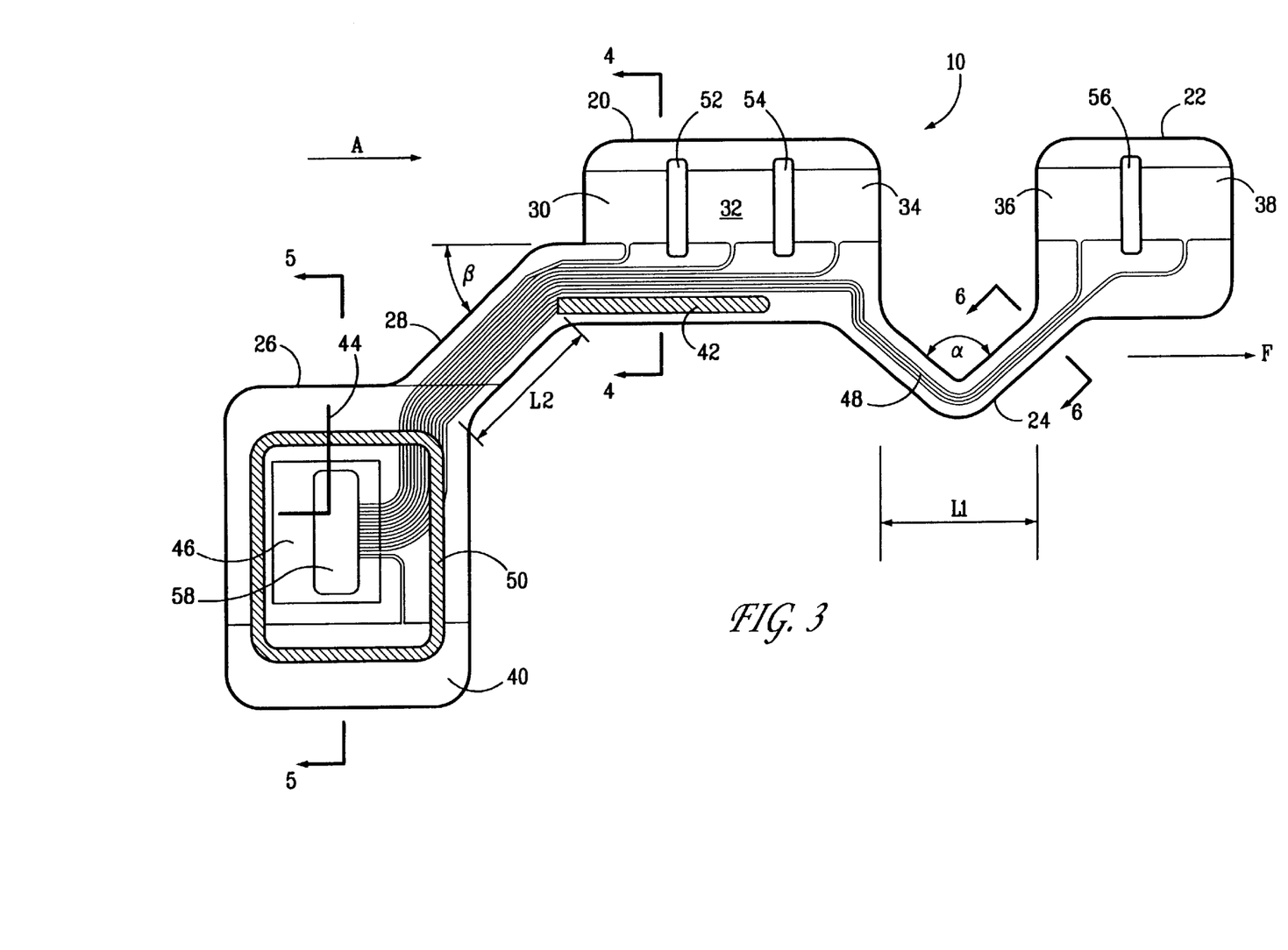
FIG. 3 is a schematic front elevation view of a device according to the invention.

FIG. 3 shows a front elevation view of a preferred embodiment of a physiological sensor device 10 according to the invention showing the face of the device which is attached to a subject in use. Device 10 comprises a first sensor region 20 for positioning in a precordial position and a second sensor region 22, connected to the first sensor region 20 by a flexible connecting membrane, yoke, or web 24. Device 10 further comprises a third sensor region 26, for positioning in the patient's axilla, attached to first sensor region 20 by a second membrane, yoke or web 28. First sensor region 20 comprises three electrode sensors 30, 32 and 34, while second region 22 comprises two electrode sensors 36 and 38. A sixth electrode sensor is provided at the bottom of third sensor region 26 in the form of electrode 40. The electrode sensors can be used to monitor such physiological parameters as heart rate, respiration and/or motion as described in the afore-mentioned co-pending application entitled "Physiological Sensor Array", U.S. patent application Ser. No. 09/292,159, and are operably in electrical contact with a patient's skin through the use of a conductive gel.

A further physiological bend sensor 42 is provided on first sensor region 20 proximal the web 28 and hence proximal a subject's pectoral muscle in use, as described later. Bend sensor 42 can be used to determine the extent of movement of a subject's chest and can comprise a sensor having a flexible non-conductive substrate onto which is mounted a strip of conductive material such as ink which in turn has a series of highly conductive areas, for example, of metal mounted on top of the conductive strip. Such sensors are, for example, available from Abrams/Gentille Entertainment Inc of New York.

A further physiological sensor is provided in the form of a temperature sensor 44 which can, for example, comprise a thermistor. Beneficially, the temperature sensor 44 can be located towards the upper end of sensor region 26 and hence close to the armpit of the wearer in use. A printed circuit board 46 is provided having suitable electronics such as the ASIC 10b and communications PIC 10c operably in communication with the various sensors via conductive tracks 48, and enabling communication to a signal transfer unit 12 via an aerial or coil antenna 50. Preferably, temperature sensor 44 and antenna 50 are directly electrically contacted with PCB 46 using suitable wiring. Also shown in FIG. 3, are a series of slots 52, 54 and 56 which pass through sensor regions 20 and 22. These slots provide an air gap separation, and hence non-conductive divide, between adjacent electrodes and also provide additional flexibility to sensor regions 20 and 22. Also shown schematically in FIG. 3 is an aperture 58 which passes through the layers of device 10 which accommodates suitable batteries and thereby enables access thereto to start the device for example by removal of an insulating strip to enable exposure of the batteries to surrounding air, in the case of Zinc Air batteries, for example.

Figure 4:
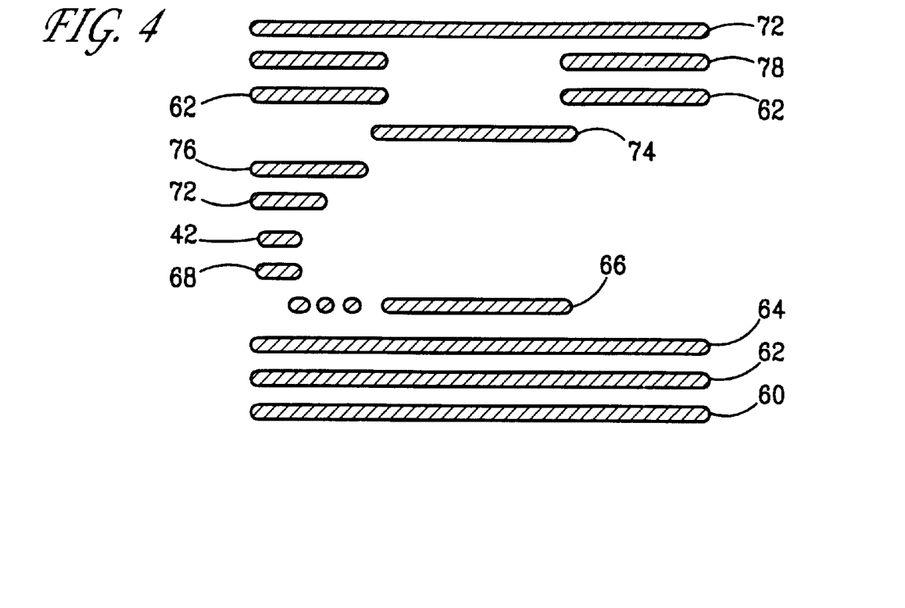
FIGS. 4, 5 and 6 are schematic exploded sectional views taken through different parts of the device shown in FIG. 3.
Figure 5:
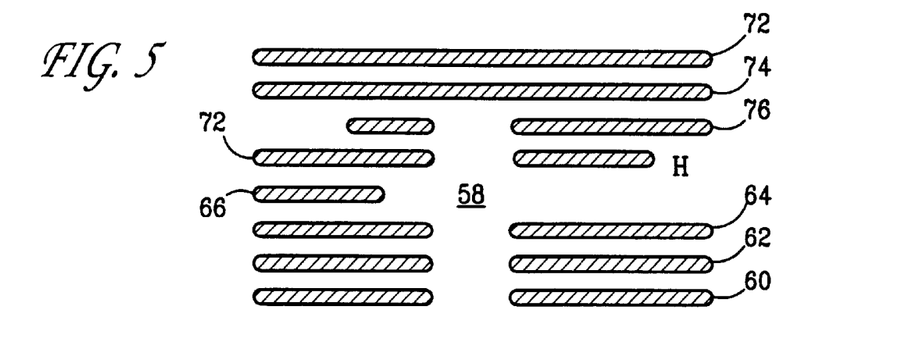
Figure 6:
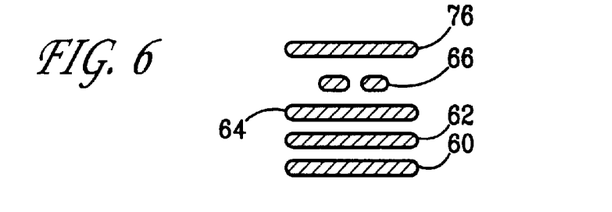

The sensor 10 is built up by various layers as illustrated in FIGS. 4, 5 and 6. FIG. 4 is a schematic sectional view through part, 4—4 (FIG. 3) of first sensor region 20. In this section, device 10 comprises a backing layer 60, for example, of a lightweight foam material which can have a fabric cover stitched on or heat bonded to its upper and/or lower surfaces to provide wear resistance. The foam 60 can be about 1 mm thick and thus provide some mechanical protection to the device 10 due to the resilience of the foam. A layer of transfer adhesive such as a pressure sensitive adhesive 62 can be provided between foam layer 60 and a substrate layer 64 for carrying conductive tracks 48. Substrate 64 is preferably a flexible non-conductive material such as PVC and can consist of for example a flexible sheet of frosty clear vinyl which is approximately 100 microns thick.

Conductive tracks 48 can be formed from a layer of conductive ink 66 printed on vinyl substrate 64. For example, a silver/silver chloride ink can be used and thus printed onto substrate 64. Preferably the ink is substantially non-polarizing.

A region of conductive adhesive 68 is provided to adhere bend sensor 42 to vinyl substrate 64 and to provide electrical connection between two electrical contacts at one end of bend sensor 42 (near web 28) with two contacts suitably provided electrically conductive tracks 48 provided at the appropriate location on substrate 64 thereby to enable communication with printed circuit board 46. Of course, the contacts between bend sensor 42 and electrically conductive tracks on substrate 64 can be provided at any position on bend sensor 42 such that a contact can be provided at each end of the bend sensor 42, for example, rather than having both contacts at one end as appropriate for the case of a U-shaped conductive track on the bend sensor 42. Electrically conductive adhesive 68 can for example be an electrically conductive tape such as provided by 3M which conducts only in the Z axis, or through the thickness of the tape only, thereby preventing electrical conduction between two adjacent electrical tracks 48.

An intermediate release liner 72 is provided which comprises at least one non-adhesive or waxy surface preventing adhesion to an adhesive layer 62. The release liner is provided to enable insertion of bend sensor 42 after construction of the various layers of device 10 and cutting thereof to form its outline shape. Release liner 72 can have one surface with a low adhesion adhesive thereby enabling relatively simple removal after insertion of bend sensor 42. A similar intermediate release layer is provided to enable insertion of printed circuit board 46 as described later.

The next layer is a second flexible backing layer 76, or flexible non-conductive intermediate layer, which is exposed in some of the upper parts of device 10 (as shown in FIGS. 4, 5 and 6) and therefore abuts the patient in use. Layer 76 can for example be a known breathable fabric layer having an underside of pressure sensitive adhesive as commonly used in medical bandaging, for example, as a backing layer to a simple plaster or BAND AID™ for an abrasion. Typically, second backing layer 76 is a tan colour and hence referred to simply as tan. The adhesive ensures layer 76 bonds to substrate 64. It should be noted that in order to show the electrical tracks 48 FIG. 3 does not show a top layer of tan 76.

The next layer shown in FIG. 4 is a conductive gel 74 which covers the main central conductive ink region 66 which forms electrode 30. Conductive gel 74 can for example be one of a range of hydrogels which enable electrical conduction between a layer of skin and conductive ink 66 thereby forming an electrode sensor. Typically the hydrogel can have a high chloride content. An example hydrogel is RG63B available from Ludlow Corporation of Chicopee, Mass. Beneficially, the layer or gel 74 can be somewhat adhesive thereby providing some adhesion to the subject in use.

Two strips of adhesive are then provided in the form of a first layer of pressure sensitive adhesive 62 and a non-conductive adhesive 78 such as a hydrocolloid. These are provided in the lateral regions (or top and bottom as seen in FIG. 3) of first sensor region 20 in order to provide adhesion to a subject's chest. The pressure sensitive adhesive 62 provides a backing to the hydrocolloid layer 78 and adheres the hydrocolloid to the surfaces of substrate 64 and or tan layer 76 as appropriate. The hydrocolloid 78 can comprise a known range of adhesives which are non-conductive and which do not generally cause any irritation to human skin. Finally, a release liner 72 is provided for storage purposes. Release liner 72 is removed in order to apply first sensor region 20 to a wearer's chest.

FIG. 5 shows a section 5—5 (FIG. 3) through third sensor region 26. Here, the outermost, or lower as shown, layer is also formed by a foam backing layer 60 which can form a continuous (albeit punctured occasionally by apertures such as slot 58) backing across the whole of device 10.

A transfer adhesive layer 62 is provided to attach substrate layer 64 to foam layer 60. Electrode 40 is formed by a region of conductive ink 66 printed on vinyl substrate 64. An intermediate release liner 72 is included over ink 66 and most of substrate 64 to enable insertion of printed circuit board 46 between vinyl substrate 64 and the underside of a tan layer 76. Preferably, a region H is provided enabling attachment of tan layer 76 to substrate 64 thereby to provide a hinge whereby the release liner 72 can be raised away from substrate layer 64 to enable insertion of printed circuit board 46 and antenna 50. As can be seen slot 58 provides a recess for batteries mounted on a printed circuit board to pass out of device 10 past layer 60. Of course, part of third region 26 (not shown) provides connection of electrical contacts on printed circuit board 46 to conductive tracks 48 and this can be achieved using a conductive adhesive tape which allows conduction through its thickness only and hence not across the adjacent tracks. Such tape is located in the appropriate position on substrate 64 above tracks 48 prior to insertion of printed circuit board 46.

Above tan layer 76 there is provided a layer 74 of conductive gel thereby enabling electrically conductive attachment of region 26 to a wearer in use. Finally, a release liner 72 is provided for storage purposes. This is removed prior to application to a subject enabling adhesion and electrical contact between the wearer and electrode 40 through hydrogel layer 74.

Second sensor region 22 is substantially the same in section as region 20 apart from the absence in this example of any other type of sensor besides electrode sensors 36 and 38. However, a simpler structure is provided for webs 24 and 28. FIG. 6 shows a schematic section 6—6 (FIG. 3) through part of web 24. It can be seen therefore that the web can be comprised of foam backing layer 60 having a transfer adhesive layer 62 enabling attachment of substrate layer 64. In this case, two electrically conductive tracks 48 are provided in the form of ink layers 66 which can be printed on substrate 64. Tan layer 76 then provides the upper surface of device 10 in the region of webs 24 and 28. Accordingly, the webs preferably do not adhere to a wearer's skin.

In order to enable suitable location of the various sensors on different subjects, it has been determined to be preferable that while each of the electrode sensors has approximately the same size, or surface area, a range of different devices is preferable, each having different dimensions and being adapted to fit different types of subjects.

Accordingly, electrode sensors of approximately 30×25 mm can be provided on regions 20 and 22, which regions are preferably separated from one another by a distance L1 of between 20 to 200 mm and more preferably between 40 and 130 mm. Three (or more) sizes of sensor device 10 can be provided for small, medium and large subjects wherein L1 is in the order of approximately 55 mm, 82.5 mm, and 110 mm respectively.

Beneficially, web 24 points downwardly in use and comprises two arms which subtend an angle alpha between 60 and 130°, more preferably 100 to 120°, and in a preferred form 115°. In a preferred form the first and second regions 20 and 22 are positioned equidistantly from the sternum and web 24 acts to enable a subject S to locate the proper positions of the sensor regions 20 and 22 by placing web 24 symmetrically over the sternum prior to attaching the first and second regions 20 and 22 to the chest. In use, third region 26 is placed just below the axilla (or armpit) of a patient and web 28 is passed over the pectoral muscle to enable first sensor region 20 to be located in a precordial position on the left side of a subject's chest while second sensor region 22 is locatable further to the right, past but proximal to the sternum. Beneficially region 26 can be loosely held in place below a wearer's left axilla using the upper left arm, before attachment due to the presence of upper release liner 72, whilst web 24 is used to locate regions 20 and 22. Alternatively region 26 can first be located in position below the left axilla first, such that the wearer then passes web 28 over the pectoral muscle and subsequently locates sensor regions 20 and 22 in position on the chest.

As described earlier, a second web 28 is provided for carrying electrical tracks 48 between regions 20 and 26, and also to provide physical integrity to the device 10. Preferably, web 28 has a mean length L2 of between 20 and 200 mm and more preferably between 50 and 110 mm. Suitable lengths L2 for a small, medium and large form of device 10 are approximately 50 mm, 75 mm, and 90 mm respectively. Preferably web 28 subtends an angle beta to the normal of the edge of first region 20 which angle is between 30 and 60° and more preferably in the order of 45°.

The shapes of web 24 and web 28 can be other than as shown in the accompanying figures. For example, the webs can be S-shaped enabling greater separation of the respectively interconnected electrode regions due to expansion of the S-shape towards a straight line configuration. Also, web 24 can be U-shaped for example. Indeed, any shape can be used which meets the functional requirements of providing a flexible connecting membrane between adjacent electrode sensor regions and also enabling electrical communication across the sensor regions.

The electrode sensors 30, 32, 34, 36 and 38 are aligned along a common transverse axis A on the device 10. This enables easier manufacture since the sides of each electrode sensor are defined by cutting as described later. Accordingly, immediately adjacent sensors such as sensor 30 and 32 are separated by a slot 52 which defines the adjacent edges of sensors 30 and 32. Similarly, slot 54 separates sensor 32 from sensor 34, and slot 56 separates sensor 36 from sensor 38.

Figure 7:
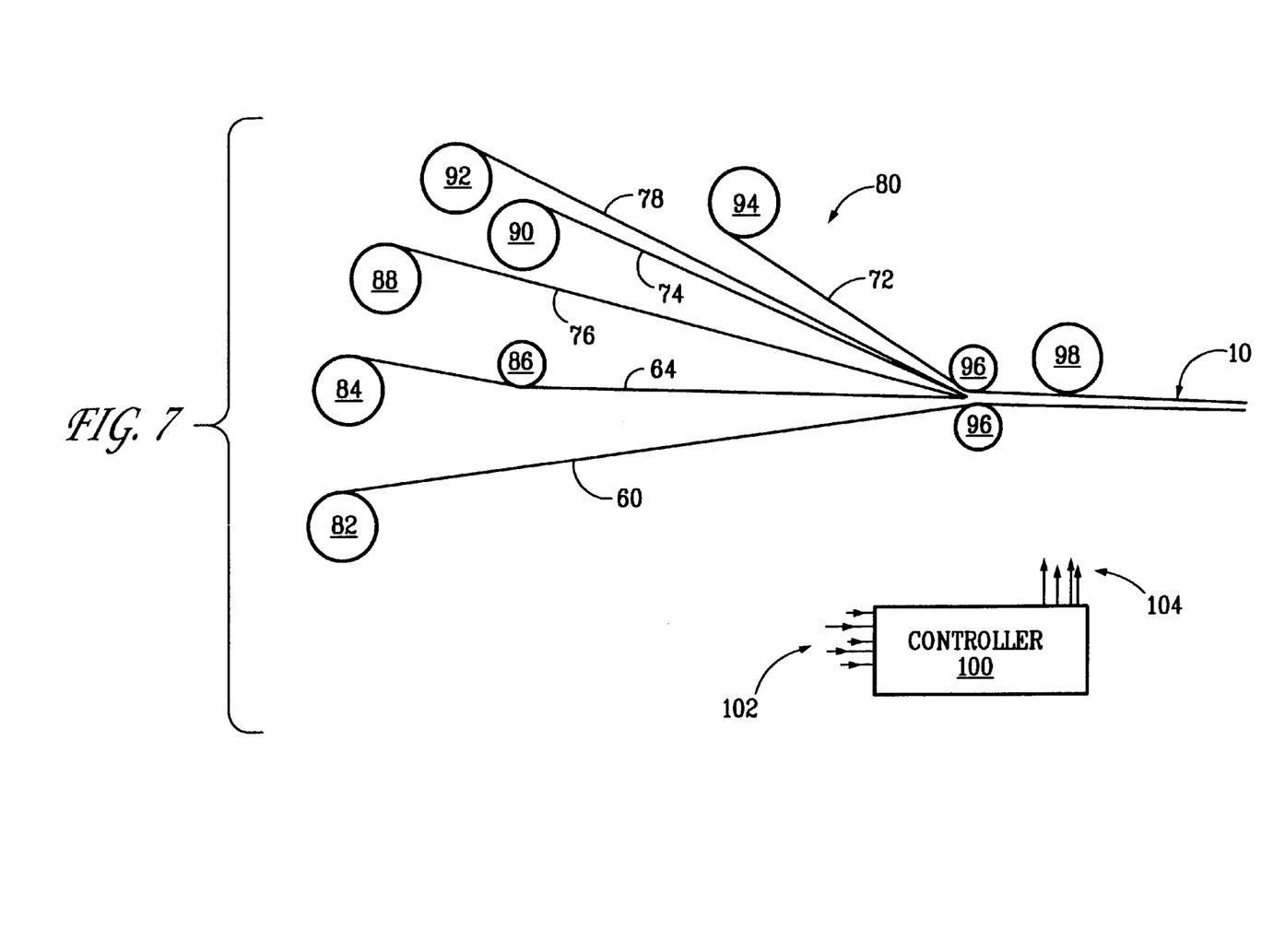
FIG. 7 is a schematic side elevation view of apparatus for manufacturing a device of the type shown in FIG. 3.

Device 10 can be manufactured using a lamination process as shown schematically in FIG. 7. A laminating machine 80 comprises a series of drums each having a roll of one or more of the layers for forming device 10. Accordingly, a drum 82 is provided having a roll of foam 60, and a second drum 84 is provided with a roll of vinyl substrate 64. Substrate 64 is passed under a printing drum 86 which prints conductive tracks 48 and electrode sensor regions 30, 32, 34, 36, 38 and 40 as appropriate at regular spaced intervals along substrate 64. Accordingly, a simple continuous pattern for the tracks and electrodes can be printed by revolution of drum 86 leaving a suitable spaced interval before the next repeat pattern. Beneficially, electrodes 30 to 38 can be printed as a single column of ink along transverse axis A of device 10 due to the movement of substrate 64 in the direction of arrow F shown in FIG. 3.

A third drum 88 is provided having a roll of tan material 76. A fourth drum 90 carries a roll of conductive gel 74 and a fifth drum 92 carries a roll of hydrocolloid 78. A sixth drum 94 is provided carrying upper release liner 72. The various layers just described can comprise a layer of transfer adhesive on a suitable surface. Alternatively, a feed of transfer adhesive can be provided from a suitably located drum on machine 80. Accordingly, the different layers are brought together or laminated at feed and compression drums 96 thereby to form a thin laminated structure ready for cutting or stamping. Prior to lamination at drums 96, the intermediate release layers 72 are inserted as appropriate in third sensor region 26 to enable later insertion of the printed circuit board 46, and a first sensor region 20 to enable later insertion of bend sensor 42.

Thus formed, die cutting drum 98 acts to cut the peripheral shape of device 10 through the different layers and to provide slots 52, 54, 56 and 58 thereby defining the individual electrode sensors 30, 32, 34, 36 and 38 from an otherwise continuously printed strip of conductive ink 66, and forming the battery aperture 58.

Laminating machine 80 can be controlled using suitable electronics to drive the various drums 82 to 98 in a synchronized manner. Accordingly, various sensors (not shown) can be used to determine the position of the different layers. Such sensors can be connected via inputs 102 to an electronic controller 100 having outputs 104 to suitable drive systems such as motors for effecting feed of the different layers from the various drums 82 to 92.

Finally, an individual physiological sensor device 10 is formed by insertion of printed circuit board 46, temperature sensor 44 and antenna 50 in region 26 and bend sensor 42 in region 20. The hydrogel layer 74 and release layer 72 can then be added separately over third sensor region 26, after the electronics described earlier. The sensor device 10 is then ready for use by removing an outer release layer 72 from the three sensor regions and applying the sensor to a user and starting up, for example, by removing an outer release layer on the batteries as described earlier.

Beneficially, the formation of device 10 through a lamination technique by feeding the layers in the direction of arrow F parallel with the transverse axis A thereof (see FIG. 3) enables a simplified manufacturing process wherein a central column of ink can be printed and subsequently cut to form different electrodes. Additionally, a relatively narrow column of hydrogel can be used to cover the printed electrode regions thereby to form the sensors. In this manner, five different sensors are formed in two sensor regions and 22. Additionally, two parallel regions of hydrocolloid can be formed at the top and bottom lateral parts of regions 20 and 22, or left and right sides as best seen in FIG. 4. Additionally, this technique provides relatively simple lateral registration of the various layers which are simply fed into the die cutter at the appropriate axial position of the rotary die cutter. Beneficially, mis-registration of for example the hydrogel and ink electrode regions 30 to 38, results in substantially the same effective surface area for each of the electrodes 30 to 38.

Moreover, the sensor device 10 according to the invention provides a very good approximation to the standard ECG lead II, as well as many other advantages as will be apparent to those skilled in the art.

According to the present invention, a sensor device is provided having any one or any combination of any of the above described features, as set forth in the following claims.

What we claim is:

1. A physiological sensor device for attachment to a mammalian subjects comprising first and second regions of sensors attachable to a subject in use, said first and second regions of sensors being separated by a flexible web adapted to enable variable separation of the first and second sensor regions from one another in use, at least one of said first and second regions of sensors including at least two sensors aligned along a common transverse axis and having respective edges separated in a direction along said common transverse axis only by a slot, said slot defining the edges of the respective sensors.

2. A physiological sensor device according to claim 1 further comprising a third region of sensors attachable to the subject, the third region being separated from one of the first region and second region by a second flexible web.

3. A physiological sensor device according to claim 2 wherein the first and second regions are adapted for application to precordial positions of the subject's chest and the third region is adapted for attachment in or proximal to the axilla of the subject.

4. A physiological sensor device according to claim 3 wherein the web has a substantially "V" shape and an apex of the "V" is centered over the sternum of the subject to position the first and second regions over the precordial positions.

5. A physiological sensor device according to claim 4 wherein the second web is adapted to pass between the subject's axilla and the subject's chest over the subject's pectoral region.

6. A physiological sensor device according to claim 2 wherein the web and second web each comprise an outer layer which contacts the subject in use and comprises a non-adhesive substance thereby to prevent attachment to the subject.

7. A physiological sensor device according to claim 1 wherein the first region and second region are separated along the common transverse axis and the electrodes of each of the first and the second regions are positioned along said common transverse axis.

8. A physiological sensor device according to claim 1 further comprising a strip of electrically conductive gel positioned along the common transverse axis and over each of the first and second sensor regions thereby to enable electrical contact between the subject and the sensors of the first and second sensor regions.

9. A physiological sensor device according to claim 8 further comprising a flexible foam backing layer.

10. A physiological sensor device according to claim 7 further comprising a flexible, non-conductive, intermediate layer disposed above the flexible foam backing layer and operably positioned intermediate the subject and the foam backing layer in use.

11. A physiological sensor device according to claim 8 further comprising two layers of non-conductive adhesive adjacent opposite sides of the layer of electrically conductive gel.

12. A physiological sensor device according to claim 11 wherein the two layers of non-conductive adhesive each comprise a strip of non-conductive adhesive and wherein the strips of adhesive are substantially parallel to one another and said common transverse axis.

13. A physiological sensor device according to claim 1 wherein the first and second sensor regions comprise electrically conductive ink printed on a flexible substrate.

14. A physiological sensor device according to claim 11 wherein the electrically conductive ink is substantially non-polarizing.

15. A physiological sensor device according to claim 11 wherein the electrically conductive ink comprises silver-silver chloride ink.

16. A physiological sensor device for attachment to a mammalian subject, comprising first and second regions of sensors attachable to a subject in use, said first and second regions of sensors being separated by a flexible web including a single substantially V-shaped portion having an apex spaced predetermined distances from said first and second regions of sensors whereby centering the apex of the V-shaped portion over the sternum of the subject causes the first and second regions to be positioned over precordial positions of the subject's chest.

17. A physiological sensor device according to claim 16 wherein the V-shaped portion is formed by two arms which subtend an angle to one another of between 60 and 130°.

18. A physiological sensor device according to claim 17 wherein the arms subtend an angle of between 100 and 120°.

19. A physiological sensor device according to claim 18 wherein the arms subtend an angle of substantially 115° to one another.

20. A physiological sensor device according to claim 16 wherein a length of separation between the first and second regions of sensors is between 20 and 200 mm.

21. A physiological sensor device according to claim 20 wherein the length of separation is between 40 and 130 mm.

22. A physiological sensor device according to claim 16 wherein the apex of the V-shaped portion points downwardly in use.

23. A physiological sensor device according to claim 16 further comprising a third region of sensors attachable to the subject, the third region being separated from one of the first region and second region by a second flexible web.

24. A physiological sensor device according to claim 23 wherein the first and second regions are adapted for application to precordial positions of the subject's chest and the third region is adapted for attachment in or proximal to the axilla of the subject.

25. A physiological sensor device according to claim 22 wherein the second web is adapted to pass between the subject's axilla and the subject's chest over the subject's pectoral region.

26. A physiological sensor device according to claim 23 wherein the second web has a neutral position when unbiased by any external forces in which neutral position the second web is disposed between the third region and one of the first region and second region at an angle of between about 30° and about 60°.

27. A physiological sensor device according to claim 23 wherein the second web is disposed at an angle of about 45° to the first region.

28. A physiological sensor device according to claim 23 wherein the length of the second web is between 20 and 200 mm.

29. A physiological sensor device according to claim 29 wherein the length of the second web is between 50 and 110 mm.

30. A physiological sensor device for attachment to a mammalian subject, comprising first, second, and third regions of sensors attachable to a subject in use, and said first and second regions of sensors being separated by a flexible web adapted to enable variable separation of the first and second sensor regions from one another for simultaneous application to the subject's precordial positions of the subject's left and right breast, respectively, and said third region of sensors being separated from one of the first region and second region by a second flexible web for simultaneous application to a position close to the subject's axilla, and one of said first, second, and third regions comprising electrical circuitry for processing physiological signals from the one or more sensors.

31. A physiological sensor device according to claim 31 wherein the electrical circuitry comprises an output transmitter for communicating the physiological signals to a remote location.

32. A physiological sensor device according to claim 32 wherein the output transmitter comprises a substantially flat coil antenna.

33. A physiological sensor device according to claim 31, wherein said web and said second web comprise a flexible non-conducting substrate and an arrangement of electrically conductive tracks formed on the substrate, the electrical circuitry being electrically connected to one or more of the electrically conductive tracks by an electrically conductive adhesive.

34. A physiological sensor device according to claim 34, further comprising a backing layer covering at least part of the arrangement of conductive tracks and attached to at least part of the flexible non-conductive substrate.

35. A physiological sensor device according to claim 34 wherein the conductive adhesive has a relatively low electrical resistance in one direction, through its thickness, and a relatively high electrical resistance orthogonal thereto.

36. A physiological sensor device according to claim 31, wherein at least two of said first, second and third regions comprise an electrode for measuring ECG and said electrodes are positioned on the subject in use so as to approximate an ECG lead II for ECG signal acquisition.

37. A physiological sensor device according to claim 31, wherein at least one of said first, second and third regions of sensors measures the subject's ECG and at least one of said first, second and third regions of sensors measures the subject's respiration.

* * * * *